US010662259B2

(12) United States Patent
Russo et al.

(10) Patent No.: US 10,662,259 B2
(45) Date of Patent: May 26, 2020

(54) GLYCOGEN-BASED WATER SOLUBILITY ENHANCERS

(71) Applicant: AZIENDE CHIMICHE RIUNITE ANGELINI FRANCESCO A.C.R.A.F. S.p.A., Rome (IT)

(72) Inventors: Vincenzo Russo, Aprilia (IT); Elisa Liberati, Rome (IT); Serena Tongiani, Genzano di Roma (IT)

(73) Assignee: AZIENDE CHIMICHE RIUNITE ANGELINI FRANCESCO A.C.R.A.F. S.p.A., Rome (IT)

( * ) Notice: Subject to any disclaimer, the term of this patent is extended or adjusted under 35 U.S.C. 154(b) by 0 days.

(21) Appl. No.: 14/780,423

(22) PCT Filed: Mar. 31, 2014

(86) PCT No.: PCT/EP2014/056451
§ 371 (c)(1),
(2) Date: Sep. 25, 2015

(87) PCT Pub. No.: WO2014/161815
PCT Pub. Date: Oct. 9, 2014

(65) Prior Publication Data
US 2016/0068615 A1 Mar. 10, 2016

(30) Foreign Application Priority Data

Apr. 5, 2013 (EP) .................................... 13162453

(51) Int. Cl.
| | | |
|---|---|---|
| *C08B 37/00* | (2006.01) |
| *A61K 47/36* | (2006.01) |
| *C08L 5/00* | (2006.01) |
| *A61K 31/715* | (2006.01) |
| *A61K 9/20* | (2006.01) |
| *A23L 33/10* | (2016.01) |
| *A23L 33/155* | (2016.01) |
| *A61K 8/31* | (2006.01) |
| *A61K 8/73* | (2006.01) |
| *A61K 31/015* | (2006.01) |
| *A61K 31/122* | (2006.01) |
| *A61Q 19/00* | (2006.01) |

(52) U.S. Cl.
CPC .......... *C08B 37/0009* (2013.01); *A23L 33/10* (2016.08); *A23L 33/155* (2016.08); *A61K 8/31* (2013.01); *A61K 8/73* (2013.01); *A61K 9/205* (2013.01); *A61K 31/015* (2013.01); *A61K 31/122* (2013.01); *A61K 31/715* (2013.01); *A61K 47/36* (2013.01); *A61Q 19/00* (2013.01); *C08L 5/00* (2013.01); *A61K 2800/10* (2013.01); *A61K 2800/56* (2013.01)

(58) Field of Classification Search
None
See application file for complete search history.

(56) References Cited

U.S. PATENT DOCUMENTS

| | | | |
|---|---|---|---|
| 4,016,354 A * | 4/1977 | Greenwood | ............ C08B 31/12 536/111 |
| 4,228,277 A * | 10/1980 | Landoll | ................. C08B 11/193 536/88 |
| 5,607,839 A * | 3/1997 | Tsubokura | .............. C12P 23/00 435/252.1 |
| 6,248,361 B1 * | 6/2001 | Johnson | ................. A61K 9/143 424/464 |
| 7,446,101 B1 | 11/2008 | Madhavi et al. | |
| 7,781,572 B2 | 8/2010 | Bartlett et al. | |
| 2004/0157207 A1 * | 8/2004 | Sommermeyer | .... A61K 9/0026 435/2 |
| 2006/0032400 A1 * | 2/2006 | Henning | ................. C08B 31/12 106/162.5 |
| 2008/0181960 A1 * | 7/2008 | Doney | ................... A61K 9/146 424/489 |
| 2011/0092393 A1 * | 4/2011 | Faust, Jr. | ................. C09K 8/52 507/90 |
| 2012/0190726 A1 | 7/2012 | Slager | |
| 2014/0378532 A1 | 12/2014 | Russo et al. | |
| 2015/0151005 A1 * | 6/2015 | Bouchemal | ........ A61K 47/4823 424/489 |

FOREIGN PATENT DOCUMENTS

| | | |
|---|---|---|
| WO | 94/03502 | 2/1994 |
| WO | 2006/040335 A1 | 4/2006 |

OTHER PUBLICATIONS

Koto, S., Haigoh, H., Shichi, S., Hirooka, M., Nakamura, T., Maru, C., . . . & Zen, S. (1995). Synthesis of Glucose-Containing Linear Oligosaccharides Having α (1→ 4) and α (1→ 6) Linkages Using Stereoselective Dehydrative Glycosylation. Bulletin of the Chemical Society of Japan, 68(8), 2331-2348.*

Narayanan, D., Nair, S., & Menon, D. (2015). A systematic evaluation of hydroxyethyl starch as a potential nanocarrier for parenteral drug delivery. International journal of biological macromolecules, 74, 575-584.*

Lindenberg, M., Kopp, S., & Dressman, J. B. (2004). Classification of orally administered drugs on the World Health Organization Model list of Essential Medicines according to the biopharmaceutics classification system. European Journal of Pharmaceutics and Biopharmaceutics, 58(2), 265-278. (Year: 2004).*

(Continued)

*Primary Examiner* — Dale R Miller
(74) *Attorney, Agent, or Firm* — Oblon, McClelland, Maier & Neustadt, L.L.P.

(57) ABSTRACT

The present invention relates to glycogen-based polymers and the use thereof for enhancing the solubility in water of lipophilic compounds, to complexes of the said glycogen-based polymers with lipophilic compounds and the use thereof for administering lipophilic compounds, and to pharmaceutical, nutraceutical, and cosmetic compositions comprising the said complexes.

11 Claims, No Drawings

(56) References Cited

OTHER PUBLICATIONS

Sergey K. Filippov, et al, "Glycogen as a Biodegradable Construction Nanomaterial for in vivo Use", Macromolecular Bioscience, vol. 12, No. 12, 2012, pp. 1731-1738.

U.S. Appl. No. 14/376,299, filed Aug. 1, 2014, US2014/0378532 A1, Russo, et al., RA/12043/PCT/US.

Sagar Pal, et al., "Synthesis, characterization and flocculation characteristics in cationic glycogen: A novel polymeric flocculant" Colloids and Surfaces A: Physicochem Eng. Aspects vol. 289, pp. 193-199 (2006), XP027995507.

International Search Report dated Jul. 3, 2014 for PCT/EP2014/056451 filed on Mar. 31, 2014.

Combined Chinese Office Action and Search Report dated Jan. 8, 2019 in Chinese Patent Application No. 201480018127.4 (with English translation), citing documents AT through AY therein, 57 pages.

Durand, A., "Synthesis of amphiphilic polysaccharides by micellar catalysis", Journal of Molecular Catalysis A: Chemical, vol. 256, 2006, Nos. 1-2; pp. 284-289.

Wesslén, K.B., et al., "Synthesis of amphiphilic amylose and starch derivatives", Carbohydrate Polymers, vol. 47, 2002, pp. 303-311 with cover page.

Covis, R., et al., "Synthesis of water-soluble and water-insoluble amphiphilic derivatives of dextran in organic medium", Carbohydrate Polymers, vol. 95, 2013, pp. 360-365.

Yu, H., et al, "Enhanced in vitro anti-cancer activity of curcumin encapsulated in hydrophobically modified starch", Food Chemistry, vol. 119, No. 2, 2010, pp. 669-674 with cover page.

Hoskins, C., et al, "A review on comb-shaped amphiphilic polymers for hydrophobic drug solubilization", Therapeutic Delivery, vol. 3, No. 1, 2012, pp. 59-79.

Rong, Z., edited, "Design, synthesis, characterization and evaluation of polysaccharide-based polymer-drug conjugates", South China University of Technology, the 1st edition, May 31, 2011, pp. 10-12 with cover pages (with partial English translation).

* cited by examiner

GLYCOGEN-BASED WATER SOLUBILITY ENHANCERS

FIELD OF THE INVENTION

The present invention relates to water solubility enhancer polymers based on glycogen, to complexes comprising the said glycogen-based polymer and at least one lipophilic compound, and to the use of the said complexes for administering lipophilic compounds. In particular, the present invention relates to derivatives of glycogen to be used as water solubility enhancer for lipophilic compounds, such as, for example, lipophilic drugs or lipophilic vitamins.

PRIOR ART

A large number of drugs and vitamins is only poorly or sparingly soluble in water so that suitable application forms like drop solutions or injection solutions are being prepared using other polar additives such as, for example, propylene glycol. If the drug molecule has basic or acidic groups there exists the further possibility of increasing the water solubility by salt formation. As a rule this results in decreased efficacy or impaired chemical stability. Due to the shifted distribution equilibrium the drug may penetrate the lipophilic membrane only slowly corresponding to the concentration of the non-dissociated fraction while the ionic fraction may be subject to a rapid hydrolytic decomposition.

The aqueous solubility of a drug is one of its most important physicochemical properties. A low aqueous solubility can potentially limit the drug absorption from the gastrointestinal tract, leading to inadequate and variable bioavailability and gastrointestinal mucosal toxicity. Besides, in the early stages of a drug pharmaceutical development, poor solubility can make difficult to conduct pharmacological, toxicological and pharmacokinetic studies.

The Biopharmaceutics Classification System or BCS divides drugs in four classes depending on their solubility and permeability properties. According to BCS, drugs having low solubility and high permeability belong to class II and drugs having low solubility and low permeability belong to class IV.

Examples of drug classes are: antinfective (antiviral, antifungal, antibiotic and antiparasitic), antirheumatic, antiallergic, anticancer, anti-inflammatory, antihypertensive, anticholesteremic, antiepileptic, analgesic, hypoglycemic, anorectic, antihypertensive, antiobesity, hormones and synthetic hormones.

Examples of class II drugs are, for example, amiodarone, atorvastatin, azithromycin, carbamazepine, carvedilol, celecoxib, chlorpromazine, cisapride, ciprofloxacin, cyclosporine, danazol, dapsone, diclofenac, diflunisal, digoxin, erythromycin, flurbiprofen, glipizide, glyburide, griseofulvin, ibuprofen, indinavir, indomethacin, itraconazole, ketoconazole, lansoprazolel, lovastatin, mebendazole, naproxen, nelfinavir, ofloxacin, oxaprozin, phenazopyridine, phenytoin, piroxicam, raloxifene, repaglinide, ritonavir, saquinavir, sirolimus, spironolactone, tacrolimus, talinolol, tamoxifen, terfenadine, and the like.

Examples of Class IV drugs are, for example, amphotericin B, chlorthalidone, chlorothiazide, colistin, ciprofloxacin, docetaxel, furosemide, hydrochlorothiazide, mebendazole, methotrexate, neomycin, paclitaxel, and the like.

Recently more than 40% of new chemical entities developed in the pharmaceutical industry are lipophilic and fail to reach market due to their poor aqueous solubility. Therefore, the improvement of drug solubility remains one of most challenging aspects of drug development process especially for oral drug delivery systems. Various approaches have been developed to overcome the issues related to poor drug solubility. Among these approaches the use of solubilizers has enjoyed widespread attention and use.

Carotenoids are used in the food industry for their nutritional and antioxidants properties. Carotenoids belong to the category of tetraterpenoids (i.e., they contain 40 carbon atoms, being built from four terpene units each containing 10 carbon atoms). Structurally, carotenoids take the form of a polyene hydrocarbon chain which is sometimes terminated by rings, and may or may not have additional oxygen atoms attached.

β-carotene is a carotenoid of relatively high molecular weight, constituted by eight isoprene units, cyclized at each end. Numerous reports suggest that β-carotene possesses biological properties implying protection against cardiovascular disorders, arteriosclerosis, degenerative eye disease as well as pathologies correlated with the age and cancer. This hydrocarbon has a water solubility clearly below 1 mg/L. Oral administration of crystalline β-carotene does not result in effective drug levels in the blood plasma.

Other useful carotenoids belonging to the class of (i) carotenes are α-carotene, γ-carotene, δ-carotene, ε-carotene, lycopene, phytoene, phytofluene, and torulene. Carotenoids further include (ii) xanthophylls, like, astaxanthin, canthaxanthin, citranaxanthin, cryptoxanthin, diadinoxanthin, diatoxanthin, dinoxanthin, flavoxanthin, fucoxanthin, lutein, neoxanthin, rhodoxanthin, rubixanthin, violaxanthin, and zeaxanthin; (iii) apocarotenoids, like abscisic acid, apocarotenal, bixin, crocetin, lonones, peridinin; (iv) vitamin A retinoids, like retinal, retinoic acid, and retinol (vitamin A); and (v) retinoid drugs, like acitretin, adapalene, alitretinoin, bexarotene, etretinate, fenretinide, isotretinoin, tazarotene, and tretinoin. Other lipophilic compounds structurally related with carotenoid are vitamins/nutritional factors such as other fat-soluble vitamins like the E, D and K vitamins.

Unfortunately, carotenoids as well as lipophilic compound structurally related with carotenoid, are not readily soluble in intestinal fluid and therefore their absorption into the body is often quite low.

Cyclodextrins have been extensively used as pharmaceutical excipients to increase the solubility of poorly water soluble drugs through inclusion complexation. Cyclodextrins are cyclic oligosaccharides consisting of 6, 7 or 8 glucopyranose units, bonded by an α-1,4-linkage, with hydrophobic interiors, usually referred to as α,β or γ cyclodextrins, respectively. In aqueous solutions, cyclodextrins are able to form inclusion complexes with many drugs by taking up the drug molecule or some lipophilic moieties of the molecule, into the central cavity. No covalent bonds are formed or broken during complex formation and the drug molecules in complex are in rapid equilibrium with free molecules in the solution.

Cyclodextrins (e.g., β-cyclodextrin) may be used specifically to increase the water solubility for parenteral injection of the structural carotenoid analogue. The use of cyclodextrins to increase the absorption and bioavailability of carotenoids is disclosed, for example, in U.S. Pat. Nos. 7,781,572 and 7,446,101, wherein nutritional supplements and soft gelatin capsules comprising a complex of cyclodextrin with carotenoids are disclosed.

In spite of previous results known in the art, compositions and methods for increasing the absorption and bioavailability of poorly water soluble drugs, carotenoids, as well as that of lipophilic compounds structurally related with carotenoids, continue to be investigated.

SUMMARY OF THE INVENTION

The Applicant has addressed the problem of developing novel solubility enhancers that can be used to increase the water solubility of lipophilic compounds, such as poorly water soluble drugs, carotenoids and compounds structurally related therewith, with the aim to improve their absorption into the gastrointestinal tract and their bioavailability, and to develop water solution for oral or injectable formulations.

Surprisingly, the Applicant has now found that glycogen can be modified so as to obtain novel glycogen-based polymers able to be used as water solubility enhancers for lipophilic compounds.

The Applicant has also surprisingly found that the novel glycogen-based polymers increased the aqueous solubility of carotenoids of several orders of magnitude with respect to the aqueous solubility of carotenoids obtainable with natural glycogen or commercially available cyclodextrins.

Advantageously, the said novel glycogen-based polymers are characterized by low cytotoxicity.

The Applicant has found that the novel glycogen-based polymers maintain the biocompatibility characteristics of the natural polymer from which they are derived.

The Applicant has also found that these novel glycogen-based polymers are capable of forming complexes with lipophilic compounds that have sizes and molecular weights within a wide range.

In a first aspect, the present invention thus relates to novel glycogen-based polymers, in particular the present invention relates to a glycogen-based polymer comprising at least one repeating unit represented by the following formula (I)

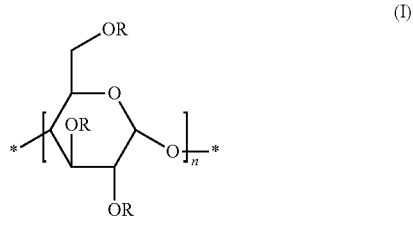

(I)

wherein
each group R, which may be identical or different, is a hydrogen atom, an alkyl group having from 1 to 12 carbon atoms, an alkenyl group having from 2 to 12 carbon atoms, an arylalkyl group having from 7 to 18 carbon atoms, or an arylalkenyl group having from 8 to 18 carbon atoms, the alkyl or alkenyl chain of said groups being optionally substituted by a hydroxyl group and/or interrupted by an oxygen atom, and the aryl residue of said groups being optionally substituted by a halogen atom, provided that at least one of said R group is different from hydrogen, and n is an integer greater than or equal to 1.

In a second aspect, the present invention relates to a complex between the glycogen-based polymers as defined above and a lipophilic compound.

According to a preferred embodiment, the said lipophilic compound is a poorly water soluble drug, a carotenoid or a lipophilic compound structurally related with carotenoid.

In a third aspect, the present invention relates to a pharmaceutical composition comprising a complex between the glycogen-based polymers as defined above and a lipophilic compound, and at least one pharmaceutically acceptable excipient.

In a fourth aspect, the present invention relates to a nutraceutical composition comprising a complex between the glycogen-based polymers as defined above and a lipophilic compound, and at least one nutraceutically acceptable excipient.

In a fifth aspect, the present invention relates to a cosmetic composition comprising a complex between the glycogen-based polymers as defined above and a lipophilic compound, and at least one cosmetically acceptable excipient.

DETAILED DESCRIPTION OF THE INVENTION

In the present description and in the claims that follow, the term "glycogen" indicates, in general, a glucose homopolymer characterized by a molecular weight of at least $2.7 \times 10^5$ daltons and by a high degree of branching, in which the glucose monomers are bonded by means of α-(1,4) bonds in the linear chains, while the branches are grafted by means of α-(1,6) bonds, generally, but without limitation, every 7-11 glucose monomers, as shown in the following formula:

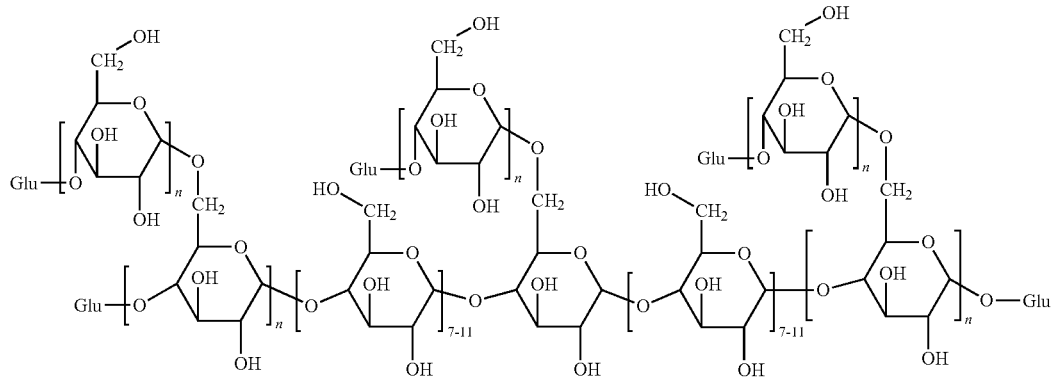

For the purposes of the present description and of the claims that follow, the wording "glycogen-based" is used to indicate that the polymer comprises the glycogen structure described above wherein one or more hydroxyl groups are derivatized to obtain the polymer according to the present invention.

For the purposes of the present description, the term "derivatized" means the formation of an ether group —OR wherein R has the meaning defined in the following formula (I).

For the purposes of the present description and of the claims that follow, the wording "repeating unit" identifies a monomer that is present at least once in the polymer according to the present invention.

For the purposes of the present description and of the claims that follow, the term "complex" indicates a product obtained by the interaction of the glycogen-based polymer according to the present invention with at least one lipophilic compound, via non-covalent interactions (for example hydrophobic, π, electrostatic, ionic or Van der Waals interactions, hydrogen bonding and the like).

In particular, the present invention relates to a glycogen-based polymer comprising at least one repeating unit represented by the following formula (I)

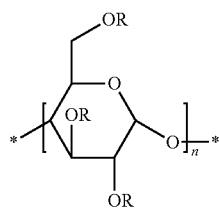

(I)

wherein
each group R, which may be identical or different, is a hydrogen atom, an alkyl group having from 1 to 12 carbon atoms, an alkenyl group having from 2 to 12 carbon atoms, an arylalkyl group having from 7 to 18 carbon atoms, or an arylalkenyl group having from 8 to 18 carbon atoms, the alkyl or alkenyl chain of said groups being optionally substituted by a hydroxyl group and/or interrupted by an oxygen atom, and the aryl residue of said groups being optionally substituted by a halogen atom, provided that at least one of said R group is different from hydrogen, and
n is an integer greater than or equal to 1.

The alkyl group represented by R is preferably an alkyl group having from 2 to 10 carbon atoms, more preferably from 2 to 9 carbon atoms, even more preferably from 2 to 8 carbon atoms, and most preferably from 4 to 8 carbon atoms.

The alkenyl group represented by R is preferably an alkenyl group having from 2 to 10 carbon atoms, more preferably from 2 to 8 carbon atoms, and most preferably from 4 to 8 carbon atoms.

The arylalkyl group represented by R is preferably an arylalkyl group having from 8 to 16 carbon atoms, more preferably from 8 to 14 carbon atoms, and most preferably from 10 to 14 carbon atoms.

The arylalkenyl group represented by R is preferably an arylalkenyl group having from 8 to 16 carbon atoms, more preferably from 8 to 14 carbon atoms, and most preferably from 10 to 14 carbon atoms.

Preferably, each group R, which may be identical or different, is a hydrogen atom; an alkyl group having from 2 to 10 carbon atoms, or an arylalkyl group having from 8 to 16 carbon atoms.

More preferably, each group R, which may be identical or different, is a hydrogen atom; an alkyl group having from 2 to 9 carbon atoms, or an arylalkyl group having from 8 to 14 carbon atoms.

Even more preferably, each group R, which may be identical or different, is a hydrogen atom; an alkyl group having from 2 to 8 carbon atoms, or an arylalkyl group having from 10 to 14 carbon atoms.

Useful examples of alkyl groups having from 1 to 12 carbon atoms include methyl, ethyl, propyl, isopropyl, n-butyl, isobutyl, sec-butyl, tert-butyl, n-pentyl, sec-pentyl, 3-pentyl, isopentyl, neopentyl, n-hexyl, sec-hexyl, neohexyl, n-heptyl, isoheptyl, sec-heptyl, n-octyl, iso-octyl, n-nonyl, iso-nonyl, n-decyl, iso-decyl, n-undecyl, n-dodecyl, and the like.

In a preferred embodiment, the alkyl group represented by R has less than 6 carbon atoms, such as for example methyl, ethyl, propyl, isopropyl, n-butyl, isobutyl, sec-butyl, tert-butyl, n-pentyl, sec-pentyl, 3-pentyl, isopentyl, neopentyl.

Useful examples of alkenyl groups having from 2 to 12 carbon atoms include ethenyl, propenyl, n-butenyl, isobutenyl, n-pentenyl, n-hexenyl, n-decenyl, and the like.

Useful examples of arylalkyl groups having from 7 to 18 carbon atoms include benzyl, phenylethyl, phenylpropyl, phenylisopropyl, phenyl-n-butyl, phenylisobutyl, phenyl-sec-butyl, phenyl-tert-butyl, phenyl-n-pentyl, phenyl-sec-pentyl, phenyl-3-pentyl, phenylisopentyl, phenylneopentyl, phenyl-n-hexyl, phenyl-sec-hexyl, phenyl-neohexyl, phenyl-n-heptyl, phenyl-isoheptyl, phenyl-sec-heptyl, phenyl-n-octyl, phenyl-isooctyl, phenyl-n-nonyl, phenyl-isononyl, phenyl-n-decyl, phenyl-isodecyl, phenyl-n-undecyl, phenyl-n-dodecyl, and the like.

Useful examples of arylalkenyl groups having from 8 to 18 carbon atoms include phenylethenyl, phenylpropenyl, phenyl-n-butenyl, phenylisobutenyl, phenyl-n-pentenyl, phenyl-n-hexenyl, phenyl-n-decenyl, and the like.

According to one embodiment of the present invention, one or more hydrogen atoms of the alkyl or alkenyl chain of the above described groups can be substituted by a hydroxyl group or an alkoxy group.

According to another embodiment of the present invention, one or more carbon atoms of the alkyl or alkenyl chain of the above described groups can be replaced by an oxygen atom.

According to a further embodiment of the present invention, one or more hydrogen atoms of the aryl residue of the above described groups can be replaced by a halogen atom, such as a chlorine atom, a fluorine atom or a iodine atom.

Useful examples of groups R are represented in Table A below.

TABLE A

*—CH$_2$—CH$_3$
*—CH$_2$—CH$_2$—CH$_3$
*—CH$_2$—CH$_2$—CH$_2$—CH$_3$
*—CH$_2$—CH$_2$—CH$_2$—CH$_2$—CH$_3$

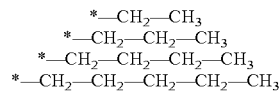

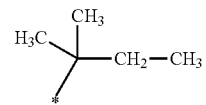

*—CH$_2$—CH$_2$—CH$_2$—CH$_2$—CH$_2$—CH$_3$

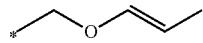

TABLE A-continued

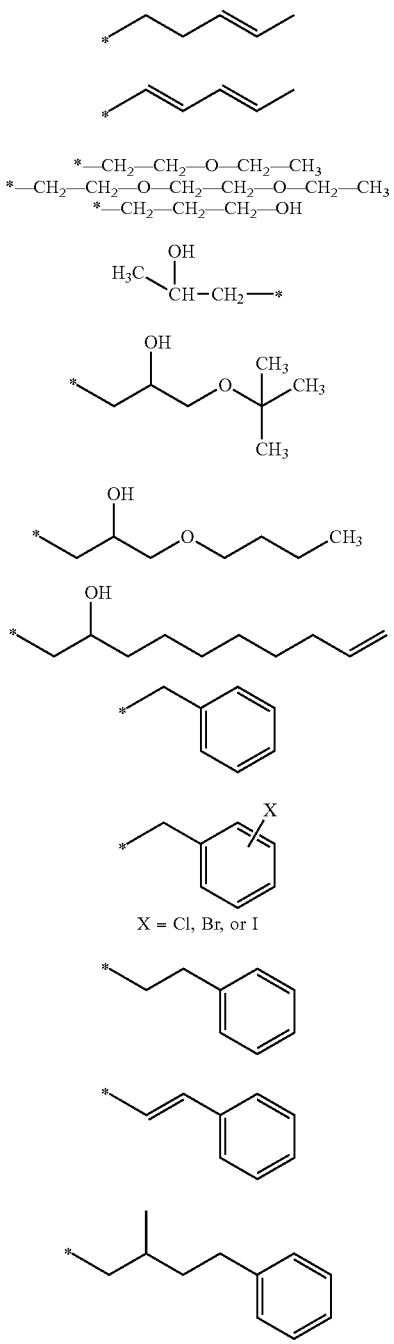

The symbol * means the link with oxygen of glycogen as showed in formula (I)

The glycogen used to prepare the glycogen-based polymers according to the present invention has a molecular weight of from about $2.7 \times 10^5$ to about $3.5 \times 10^6$ daltons.

The glycogen-based polymers according to the present invention has a molecular weight substantially similar or higher than the molecular weight of the starting glycogen, due to the substitution of part of the hydrogens of the hydroxyl group of the glucose residues with the group R as defined herein.

The glycogen-based polymers according to the present invention have the same structural backbone of the starting glycogen.

The glycogen used to prepare the glycogen-based polymers according to the present invention may be obtained according to one of the methods known in the art.

Preferably, the glycogen is prepared as described in international patent application WO 94/03502.

Preferably, the said glycogen is obtained from the species *Mytilus edulis* and *Mytilus galloprovincialis*.

Other sources of glycogen that may be used for the purposes of the present invention include shellfish, such as oysters and *Crepidula fornicata*, and the glycogen-rich organs of vertebrate animals, such as liver and muscles.

Preferably, the said glycogen is substantially free of compounds containing nitrogen and reducing sugars. As used in the present description and in the claims that follow, the expression "substantially free of compounds containing nitrogen and reducing sugars" indicates that the nitrogen content is less than 60 ppm, measured by means of the Kieldahl method, and the content of reducing sugars is less than 0.25%, measured by means of the method of F. D. Snell and Snell ("*Colorimetric Methods of Analysis*", New York, 1954, vol. III, p. 204).

Preferably, the glycogen used according to the present invention is also characterized by a carbon content from about 44% to about 45%, a molecular weight of about $(2.5\pm0.1)\times10^6$ daltons measured by a viscosimetric method and an optical rotation $(\alpha)_D^{20}$ of $197\pm2.0$ (c=1, in water).

More preferably, the glycogen used according to the present invention is Polglumyt™ glycogen, produced by Aziende Chimiche Riunite Angelini Francesco A.C.R.A.F. S.p.A.

A person skilled in the art will readily understand that the present invention is not directed towards novel classes of compounds with therapeutic efficacy per se. Rather, the present invention relates to the use of a glycogen-based polymer as described previously for forming a complex with at least one lipophilic compound.

In a second aspect, the present invention relates to a complex between a glycogen-based polymer and a lipophilic compound, in which the said glycogen-based polymer comprises at least one repeating unit (I) as described previously.

According to a preferred embodiment, the said lipophilic compound is a poorly water soluble drug, a carotenoid or a lipophilic compound structurally related with carotenoid.

Preferably, the said poorly water soluble drug is selected from the group consisting of (i) BCS class II and (ii) BCS class IV drugs. Under the Biopharmaceutics Classification System (BCS) Guidance, a drug substance is considered low soluble, and then classified in BCS class II or IV, when the highest dose strength is not soluble in less than 250 ml water over a pH range of 1 to 7.5.

Advantageously, useful poorly water soluble drugs belonging to the BCS class II are amiodarone, atorvastatin, azithromycin, carbamazepine, carvedilol, celecoxib, chlorpromazine, cisapride, ciprofloxacin, cyclosporine, danazol, dapsone, diclofenac, diflunisal, digoxin, erythromycin, flurbiprofen, glipizide, glyburide, griseofulvin, ibuprofen, indinavir, indomethacin, itraconazole, ketoconazole, lansoprazolel, lovastatin, mebendazole, naproxen, nelfinavir, ofloxacin, oxaprozin, phenazopyridine, phenytoin, piroxicam, raloxifene, repaglinide, ritonavir, saquinavir, sirolimus, spironolactone, tacrolimus, talinolol, tamoxifen, terfenadine, and the like.

Advantageously, useful poorly water soluble drugs belonging to the BCS class IV are amphotericin B, chlorthalidone, chlorothiazide, colistin, ciprofloxacin, docetaxel, furosemide, hydrochlorothiazide, mebendazole, methotrexate, neomycin, paclitaxel, and the like.

Preferably, the said carotenoid or lipophilic compound structurally related with carotenoid is selected from the group consisting of (i) carotenes, (ii) xanthophylls, (iii) apocarotenoids, (iv) Vitamin A retinoids, (v) retinoid drugs, and (vi) other lipophilic vitamins/nutritional factors.

Advantageously, useful carotenoids belonging to the class of (i) carotenes are α-carotene, β-carotene, γ-carotene, δ-carotene, ε-carotene, lycopene, phytoene, phytofluene, and torulene.

Carotenoids further include (ii) xanthophylls, like antheraxanthin, astaxanthin, canthaxanthin, citranaxanthin, cryptoxanthin, diadinoxanthin, diatoxanthin, dinoxanthin, flavoxanthin, fucoxanthin, lutein, neoxanthin, rhodoxanthin, rubixanthin, violaxanthin, and zeaxanthin; (iii) apocarotenoids, like abscisic acid, apocarotenal, bixin, crocetin, Ionones, peridinin; (iv) Vitamin A retinoids, like retinal, retinoic acid, and retinol (vitamin A); and (v) retinoid drugs, like acitretin, adapalene, alitretinoin, bexarotene, etretinate, fenretinide, isotretinoin, tazarotene, and tretinoin.

Other lipophilic compounds structurally related with carotenoids are (vi) vitamins/nutritional factors such as other fat-soluble vitamins like the E, D and K vitamins.

According to a preferred embodiment, the said complex comprises an amount of the said lipophilic compound of between 0.1% and 90% by weight relative to the weight of the said glycogen-based polymer.

Preferably, the said complex comprises an amount of the said lipophilic compound of between 0.5% and 70% by weight relative to the weight of the said glycogen-based polymer.

More preferably, the said complex comprises an amount of the said lipophilic compound of between 1% and 50% by weight relative to the weight of the said glycogen-based polymer.

The complex between a glycogen-based polymer and a lipophilic compound may advantageously be prepared as a pharmaceutical composition.

In a third aspect, the present invention relates to a pharmaceutical composition comprising a complex between a glycogen-based polymer and a lipophilic compound, and at least one pharmaceutically acceptable excipient, in which the said glycogen-based polymer comprises at least one repeating unit represented by the formula (I), described previously.

According to a preferred embodiment, the said lipophilic compound is a poorly water soluble drug, a carotenoid or a lipophilic compound structurally related with carotenoid.

Preferably, the said poorly water soluble drug is selected from the group consisting of (i) BCS class II and (ii) BCS class IV drugs, as described above.

Preferably, the said carotenoid or a lipophilic compound structurally related with carotenoid is selected from the group consisting of (i) carotenes, (ii) xanthophylls, (iii) apocarotenoids, (iv) Vitamin A retinoids, (v) retinoid drugs, and (vi) other lipophilic vitamins/nutritional factors, as described above.

The term "excipient" means any agent known in the art that is suitable for preparing a pharmaceutical form.

Examples of excipients that are suitable according to the present invention are: preservatives, stabilizers, surfactants, osmotic pressure-regulating salts, emulsifiers, sweeteners, flavourings, dyes and the like.

The said pharmaceutical composition may be prepared in unit dosage form according to methods known in the art.

Preferably, the said pharmaceutical composition is for injectable use, such as for instance an aqueous solution, suspension or emulsion, or may be in the form of a powder to be reconstituted for the preparation of an aqueous solution, suspension or emulsion for intravenous, intramuscular, subcutaneous, transdermal or intraperitoneal administration.

Alternatively, the said pharmaceutical composition may be, for example, in the form of a tablet, a capsule, coated tablets, granules, solutions and syrups for oral administration; medicated plasters, solutions, pastes, creams or pomades for transdermal administration; suppositories for rectal administration; a sterile solution for aerosol administration; for immediate and sustained release.

In a fourth aspect, the present invention relates to a nutraceutical composition comprising a complex between the glycogen-based polymers as defined above and a lipophilic compound, and at least one nutraceutically acceptable excipient.

According to a preferred embodiment, the said lipophilic compound is a carotenoid or a lipophilic compound structurally related with carotenoid, as described above.

Nutraceutical compositions (e.g. foods or naturally occurring food supplements intended for human ingestion, and thought to have a beneficial effect on human health) are commonly used for their preventative and medicinal qualities.

Such nutraceutical compositions may comprise a single element, or, alternatively, may comprise of complex combinations of substances resulting in a nutraceutical that provides specific benefits.

The nutraceutical compositions may be in the form of a complete foodstuff, a food supplement, a nutritional solution for gastro-enteric administration, for example for enteric feeding administered through a naso-gastric and naso-enteric tube, a nutritional solution for parenteral administration, or a foodstuff or supplement for diabetic individuals.

The nutraceutically acceptable excipient to be used into the nutraceutical compositions according to the present invention may improve its appearance, pleasantness and preservation, such as for example colouring agents, preservatives, antioxidants, acidity regulators, thickeners, stabilisers, emulsifiers, flavour enhancers, flavourings, humectants and sweeteners.

In a fifth aspect, the present invention relates to a cosmetic composition comprising a complex between the glycogen-based polymers as defined above and a lipophilic compound, and at least one cosmetically acceptable excipient.

According to a preferred embodiment, the said lipophilic compound is a carotenoid or a lipophilic compound structurally related with carotenoid, as described above.

The cosmetic composition according to this invention comprises liquid or semi-solid formulations.

The liquid formulations for cosmetic use according to this invention comprise solutions, emulsions, microemulsions, lotions, foams, milks, oils, relaxants or suspensions of widely varying viscosity.

The liquid formulations may for example be aqueous solutions, water-alcohol solutions, solutions in oil, emulsions obtained by dispersing an oily phase in an aqueous phase (oil-in-water) or vice-versa an aqueous phase in an oily phase (water-in-oil), and suspensions obtained by dispersing a dispersed phase comprising solid particles in a dispersing medium generally represented by an aqueous or oily liquid having a particular viscosity.

The semi-solid formulations for cosmetic use according to this invention comprise creams, gels, ointments, pastes, cream-gels, sticks and waxes.

The formulations for cosmetic use of this invention may comprise various cosmetically-acceptable additives or vehicles which are useful in the preparation of cosmetic products and known to those skilled in the art such as, for example, emulsifiers, hydrating agents, solvents, emollients, stabilisers, viscosity agents, preservatives, lubricants, sequestrating or chelating agents, fillers, fragrances, perfumes, absorbants, colouring agents and opacifiers, antioxidants, plant extracts and oils, vitamins, foaming substances, essential oils, keratin-active substances and amino acids.

The examples that follow are intended to illustrate the present invention without, however, limiting it in any way.

EXAMPLES

Example 1

Preparation of Glycogen-Based Polymers Comprising the Unit (I)

Polglumyt® glycogen (5 g; 30.86 mmol of glucose) was dried under vacuum at 60° C. for several days to remove the physically adsorbed water. After cooling to room temperature, under nitrogen atmosphere, the polymer was dissolved in dry dimethylsulfoxide (100 mL) in a two-necked round-bottomed flask, equipped with a magnetic stirrer and a reflux condenser.

Sodium hydride (NaH) was then added and the mixture was stirred at room temperature for 1 hour. Then, the reagent (R-X) was added, and the mixture was stirred at room temperature overnight. The amounts of sodium hydride and reagents R-X, expressed as mmol, are reported in Table 1.

The next day, 300 mL of ethanol were added and the mixture was centrifuged. The precipitate was recovered and washed twice with 100 ml of ethanol, centrifuged and the solid product was recovered. The solid obtained was dissolved in water (150 mL) and finally subjected to dialysis in regenerated cellulose tubes (cut-off 15,000) against distilled water until the conductivity was constant (equal to about 2-3 µS). The solution obtained was filtered through a 0.45 µm filter, concentrated under vacuum and finally freeze-dried. The synthetic yields are collated in Table 1.

TABLE 1

| Polymer | AP code | mmol of NaH | Reagent (RX) | mmol of RX | Yield % |
|---|---|---|---|---|---|
| 1 | AP104 | 46.30 | 1-Chloroexane | 3.09 | 75 |
| 2 | AP105 | 61.73 | 1-Chloroexane | 6.17 | 75 |

TABLE 1-continued

| Polymer | AP code | mmol of NaH | Reagent (RX) | mmol of RX | Yield % |
|---|---|---|---|---|---|
| 3 | AP106 | 84.50 | 1-Chloroexane | 10.80 | 80 |
| 4 | AP107 | 105.73 | 1-Chloroexane | 15.43 | 65 |
| 5 | AP110 | 105.73 | 1-Chloroexane | 30.86 | 70 |
| 6 | AP111 | 123.46 | 1-Chloroexane | 46.29 | 75 |
| 7 | AP112 | 46.29 | Benzyl bromide | 3.09 | 75 |
| 8 | AP113 | 61.73 | Benzyl bromide | 6.17 | 65 |

Polglumyt® glycogen (5 g; 30.86 mmol of glucose) was dissolved in 31 mL of 1N NaOH in a two-necked round-bottomed flask, equipped with a magnetic stirrer and a reflux condenser. Once the dissolution was complete, the mixture was heated to 70° C. and stirred for 2 hours.

Then, the reagent (R-X) was added, and the mixture was stirred at 70° C. overnight. The amounts of reagent R-X, expressed as mmol of reagent, are reported in Table 2.

The next day, the heating was stopped and the mixture was allowed to cool to room temperature. The crude reaction product was then poured slowly into 200 mL of acetone. Once the addition was complete, the suspension obtained was stirred for about 30 minutes. After stopping the stirring, the mixture was left to sediment until separation of the supernatant and the precipitate was recovered.

The supernatant was discarded and the precipitate obtained was washed twice with acetone (100 mL). The solid thus obtained was filtered off, dissolved in 200 mL of distilled water, brought to neutral pH with 1N HCl solution and finally subjected to dialysis in regenerated cellulose tubes (cut-off 15,000) against distilled water until the conductivity was constant (equal to about 2-3 µS). The solution obtained was filtered through a 0.45 µm filter, concentrated under vacuum and finally freeze-dried. The synthetic yields are collated in Table 2.

TABLE 2

| Polymer | AP code | Reagent (RX) | mmol of (RX) | Yield % |
|---|---|---|---|---|
| 9 | AP2 | tert-Butyl glycidyl ether | 30.86 | 70 |
| 10 | AP4 | Butyl glycidyl ether | 30.86 | 75 |
| 11 | AP15 | 1,2-Epoxy-9-decene | 30.86 | 75 |
| 12 | AP22 | 3-Chloro-1-propanol | 30.86 | 70 |

The following Table 3 summarizes the $^1$H-NMR (D2O) or IR data of the compounds 1 to 12 synthesized above.

TABLE 3

| Polymer | AP code | R | $^1$H-NMR (D$_2$O) or IR data |
|---|---|---|---|
| 1 | AP104 | *∧∧∧CH$_3$ | $^1$H-NMR: δ ppm: 1.22 (CH$_3$—CH$_2$), 1.64 (CH$_3$—CH$_2$—CH$_2$—CH$_2$), 1.90 (—CH$_2$—CH$_2$—O—) 3.65-4.5 (multiplet), 5.25-5.85 (multiplet H anomeric) |
| 2 | AP105 | *∧∧∧CH$_3$ | $^1$H-NMR: δ ppm: 1.17 (CH$_3$—CH$_2$), 1.59 (CH$_3$—CH$_2$—CH$_2$—CH$_2$), 1.86 (—CH$_2$—CH$_2$—O—) 3.65-4.5 (multiplet), 5.25-5.85 (multiplet H anomeric) |
| 3 | AP106 | *∧∧∧CH$_3$ | $^1$H-NMR: δ ppm: 1.22 (CH$_3$—CH$_2$), 1.64 (CH$_3$—CH$_2$—CH$_2$—CH$_2$), 1.91 (—CH$_2$—CH$_2$—O—) 3.65-4.5 (multiplet), 5.25-5.85 (multiplet H anomeric) |

TABLE 3-continued

| Polymer | AP code | R | ¹H-NMR (D₂O) or IR data |
|---|---|---|---|
| 4 | AP107 | 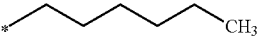 | ¹H-NMR: δ ppm: 1.22 (CH₃—CH₂), 1.64 (CH₃—CH₂—CH₂—CH₂), 1.91 (—CH₂—CH₂—O—) 3.65-4.5 (multiplet), 5.25-5.85 (multiplet H anomeric) |
| 5 | AP110 | 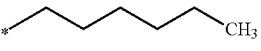 | ¹H-NMR: δ ppm: 1.21 (CH₃—CH₂), 1.64 (CH₃—CH₂—CH₂—CH₂), 1.91 (—CH₂—CH₂—O—) 3.65-4.5 (multiplet), 5.25-5.85 (multiplet H anomeric) |
| 6 | AP111 | 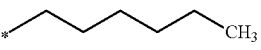 | ¹H-NMR: δ ppm: 1.21 (CH₃—CH₂), 1.63 (CH₃—CH₂—CH₂—CH₂), 1.91 (—CH₂—CH₂—O—) 3.65-4.5 (multiplet), 5.25-5.85 (multiplet H anomeric) |
| 7 | AP112 | 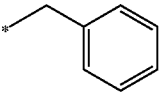 | ¹H-NMR: δ ppm: 3.6-4.5 (multiplet), 4.90-6.05 (multiplet H anomeric), 7.76 (H aromatic) |
| 8 | AP113 | 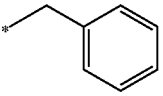 | ¹H-NMR: δ ppm: 3.6-4.5 (multiplet), 4.90-6.05 (multiplet H anomeric), 7.75 (H aromatic) |
| 9 | AP2 | 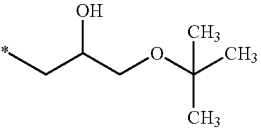 | ¹H-NMR: δ ppm 1.26 (CH₃), 3.35-4.1 (multiplet), 5.25-5.85 (multiplet H anomeric) |
| 10 | AP4 | 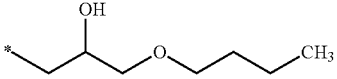 | ¹H-NMR: δ ppm 0.91 (CH₃), 1.41 (CH₃—CH₂—), 1.59 (CH₃—CH₂—CH₂—) 3.25-4.5 (multiplet), 5.25-5.85 (multiplet H anomeric) |
| 11 | AP15 | 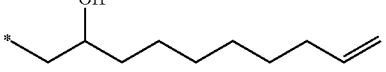 | ¹H-NMR: δ ppm 1.0-2.6 (multiplet), 3.45-4.65 (multiplet), 5.05-6.25 (multiplet) |
| 12 | AP22 | 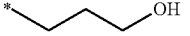 | ¹H-NMR: δ ppm 1.84 (—CH₂—CH₂—CH₂—), 3.25-4.25 (multiplet), 5.25-5.80 (multiplet H anomeric) |

Example 2

Evaluation of Solubility Enhancement

Twelve water solutions containing 5 mg/mL of each compound synthesized in example 1 were prepared. The suspensions were left under stirring for 24 hours. Solutions A to N were obtained.

Similarly, four water solutions containing 5 mg/mL of the compound of the following table 4 were prepared. The suspensions were left under stirring for 24 hours. Solutions O to R were obtained.

TABLE 4

| Compound | Name |
|---|---|
| 13 | natural glycogen (Polglumyt ®) |
| 14 | γ-cyclodextrin (CAVAMAX W8) |
| 15 | β-cyclodextrin (CAVAMAX W7) |
| 16 | HP-β-cyclodextrin (CAVASOL W7 HP) |

An excess amount of β-carotene (5 mg/mL) was added to 1 mL of each solution A to R. The suspension was mixed using a laboratory shaker at room temperature for 24 hours. The concentration (mg/mL) of solubilized β-carotene was determined by HPLC analysis. The sample was prepared for chromatographic analysis by filtering through a 0.45 μm MCE filter.

The chromatographic system (Waters) consisted of a solvent delivery module (Model Alliance e2695), a variable-wavelength UV spectrophotometric detector (Model 2489) and a chromatographic data control and acquisition system (Empower). An X-Bridge™ Shield RP18 column (4.6×150 mm) was used. A suitable HPLC analytical method was developed for quantitating the amount of drug in solution.

Elution was performed isocratically with acetonitrile/methylene chloride at a weight ratio of 89:11 at a flow rate of 1.5 mL/min. The absorbance was monitored at 450 nm and the injection volume was 5 μL. In these chromatographic conditions, β-carotene was eluted in about 5.5 minutes.

For the calibration curve, β-carotene standard solutions were prepared by diluting with dimethylsulfoxide a stock solution prepared as follows: 1.145 mg of β-carotene were solubilized in 550 μL of methylene chloride and added to 18.32 mL of dimethylsulfoxide (β-carotene final concentration was 0.0607 mg/mL). The stock solution was diluted with dimethylsulfoxide to obtain standard solutions with decreasing concentration, until to a β-carotene concentration of $9.5*10^{-4}$ mg/mL. The calibration curve was constructed using analyte peak area ratio versus concentration of the standard solutions, subjected to chromatography under the same conditions of the samples.

An appropriate dilution of each sample was made with dimethylsulfoxide, such that β-carotene final concentration was within the linear portion of the standard curve, prior to injection onto the HPLC column.

The amount of β-carotene in mg/mL was calculated by introducing the analyte peak area in the calibration curve fit-equation and multiplying the result by the dilution factor.

Aqueous solubility (mg/mL) of β-carotene in the presence of the compounds of the present invention (samples 1 to 12) and in the presence of natural glycogen (sample 13) or cyclodextrins (samples 14 to 16) is reported in Table 5.

TABLE 5

| Solution | Compound | Solubility |
| --- | --- | --- |
| A | 1 | 0.81 |
| B | 2 | 0.76 |
| C | 3 | 0.54 |
| D | 4 | 0.55 |
| E | 5 | 0.90 |
| F | 6 | 0.44 |
| G | 7 | 0.53 |
| H | 8 | 0.59 |
| I | 9 | 0.07 |
| L | 10 | 0.13 |
| M | 11 | 0.18 |
| N | 12 | 0.01 |
| O | 13 | 0.00 |
| P | 14 | 0.01 |
| Q | 15 | 0.00 |
| R | 16 | 0.05 |

Hexyl and benzyl glycogen derivatives (compounds 1 to 8) caused the highest increase in the solubility of β-carotene. They increased the drug aqueous solubility up to several orders of magnitude compared to cyclodextrins. The results were confirmed by the visual aspect of solutions. Mixing β-carotene with hexyl and benzyl glycogen derivatives an orange, clear solution was achieved while cyclodextrin solutions were colorless. Only a pale pink color in HP-β-cyclodextrin solution (sample 16) was observed, but the color intensity was lower than that observed with the solution of the compounds of the present invention.

Natural glycogen did not improve the solubility of β-carotene. Compounds 10 and 11 caused a lower increase in the solubility of β-carotene, and compounds 9 and 12 caused the slowest increase in the solubility of β-carotene.

These results demonstrated that the compounds of the present invention are able to enhance the solubility of β-carotene.

Example 3

Evaluation of Solubility Enhancement

An excess amount of astaxanthin (1 mg/mL) was added to 1 mL of each solution A to R, prepared as for example 2. The suspension was mixed using a laboratory shaker at room temperature for 24 hours. The concentration (mg/mL) of solubilized astaxanthin was determined by HPLC analysis. The sample was prepared for chromatographic analysis by filtering through a 0.45 μm MCE filter.

The chromatographic system (Waters) consisted of a solvent delivery module (Model Alliance e2695), a variable-wavelength UV spectrophotometric detector (Model 2489) and a chromatographic data control and acquisition system (Empower). An X-Bridge™ Shield RP18 column (4.6×150 mm) was used. A suitable HPLC analytical method was developed for quantitating the amount of astaxanthin in solution.

Elution was performed by gradient elution using a mixture of acetonitrile/tetrahydrofuran at a weight ratio of 70:30 in channel A and water in channel B. The flow rate was 1 mL/min. The gradient elution parameters were as follows:

| Time (min) | % A | % B | Note |
| --- | --- | --- | --- |
| 0:00-7:00 | 75 | 25 | Isocratic elution |
| 7:00-8:00 | 75→50 | 25→50 | Gradient elution in 1 minute |
| 8:00-12:00 | 50 | 50 | Isocratic elution |
| 12:00-13:00 | 50→75 | 50→25 | Gradient elution in 1 minute |
| 13:00-15:00 | 75 | 25 | Isocratic elution |

The absorbance was monitored at 489 nm and the injection volume was 6 μL. In these chromatographic conditions, astaxanthin was eluted in about 4.0 minutes.

For the calibration curve, astaxanthin standard solutions were prepared by diluting with dimethylsulfoxide a stock solution prepared as follows: 4 mg of astaxanthin were solubilized in 4 mL of dimethylsulfoxide. The stock solution was diluted with dimethylsulfoxide to obtain standard solutions with decreasing concentration, until to an astaxanthin concentration of $9.7*10^{-4}$ mg/mL. The calibration curve was constructed using analyte peak area ratio versus concentration of the standard solutions, subjected to chromatography under the same conditions of the samples.

An appropriate dilution of each sample was made with dimethylsulfoxide, such that astaxanthin final concentration was within the linear portion of the standard curve, prior to injection onto the HPLC column.

The amount of astaxanthin in mg/mL was calculated by introducing the analyte peak area in the calibration curve fit-equation and multiplying the result by the dilution factor.

Aqueous solubility (mg/mL) of astaxanthin in the presence of the compounds of the present invention (samples 1 to 12) and in the presence of natural glycogen (sample 13) or cyclodextrins (samples 14 to 16) is reported in Table 6.

TABLE 6

| Solution | Compound | Solubility |
| --- | --- | --- |
| A | 1 | 0.0371 |
| B | 2 | 0.0504 |
| C | 3 | 0.0455 |
| D | 4 | 0.0554 |
| E | 5 | 0.0595 |
| F | 6 | 0.0712 |
| G | 7 | 0.0271 |
| H | 8 | 0.0336 |
| I | 9 | 0.0221 |
| L | 10 | 0.0331 |
| M | 11 | 0.0444 |
| N | 12 | 0.0198 |
| O | 13 | 0.0079 |
| P | 14 | 0.0012 |
| Q | 15 | 0.0005 |
| R | 16 | 0.0007 |

All tested compounds increased the astaxanthin aqueous solubility up to several orders of magnitude compared to cyclodextrins. The results were confirmed by the visual aspect of solutions. Mixing astaxanthin with glycogen derivatives a red, clear solution was achieved while cyclodextrin solutions were colorless.

Natural glycogen did not improve the solubility of astaxanthin. In this case, compounds 9 to 12 showed results comparable with those of compounds 1 to 8.

These results demonstrated that the compounds of the present invention are able to enhance the solubility of astaxanthin.

Example 4

Evaluation of Viscosity

Twelve water solutions containing 10 mg/mL (1% w/w) of each compound synthesized in example 1 were prepared. The suspensions were left under stirring for 24 hours. Solutions A' to N' were obtained.

The viscosity measurements were performed using a Bohlin Gemini 150 rotary rheometer piloted by the Bohlin R6 40.5.32 software, equipped with cone-plate geometry 2°/55 mm, thermostatically maintained with a Peltier Bohlin instrument at 25° C. and performed in "controlled stress" mode in a shear stress range of from 1 to 5 Pa. By way of example, Table 7 reports the viscosity values of the various derivatives measured at a single stress value (2.5 Pa).

The solutions A' to N' showed very low viscosity values, all around 1-2 mPa*s, as summarized in the following Table 7.

Such low viscosity values of the solutions obtained with the compounds of the present invention make them ideal solubility enhancers for injectable formulations.

TABLE 7

| Solution | Compound | Viscosity at 2.5 Pa (mPa*s) |
|---|---|---|
| A' | 1 | 1.90 |
| B' | 2 | 1.94 |
| C' | 3 | 1.89 |
| D' | 4 | 1.95 |
| E' | 5 | 1.96 |
| F' | 6 | 1.95 |
| G' | 7 | 2.01 |
| H' | 8 | 1.95 |
| I' | 9 | 1.93 |
| L' | 10 | 1.94 |
| M' | 11 | 1.95 |
| N' | 12 | 1.93 |

Example 5

The following tables 8 to 10 show specific examples of compositions according to the present invention.

TABLE 8

Pharmaceutical formulation
Tablet

| Ingredient | Unit | Amount |
|---|---|---|
| Beta-Carotene | mg | 10 |
| Compound 1 | mg | 90 |
| Microcrystalline Cellulose | mg | 160 |
| Starch | mg | 39 |
| Magnesium Stearate | mg | 1 |

TABLE 9

Nutraceutical formulation
Powder for dissolution in about 100 mL of water

| Ingredient | Unit | Amount |
|---|---|---|
| Beta-Carotene | mg | 30 |
| Compound 1 | mg | 200 |
| Maltodextrin | g | 20 |
| Dextrose | g | 10 |
| Proteins | g | 10 |
| Glutamine | g | 2 |
| Magnesium | mg | 25 |
| Sodium | mg | 345 |
| Potassium | mg | 145 |
| Chlorides | mg | 130 |
| Glucosamine | mg | 200 |
| Vitamin B1 | % RDA | 50% |
| Vitamin B2 | % RDA | 50% |
| Vitamin B5 | % RDA | 50% |
| Vitamin B6 | % RDA | 50% |
| Vitamin B12 | % RDA | 50% |
| Vitamin A | % RDA | 50% |
| Vitamin C | % RDA | 200% |
| Vitamin E | % RDA | 200% |

RDA = Recommended Dietary Allowance

TABLE 10

Cosmetic formulation
Cream, 100 g

| Ingredient | Unit | Amount |
|---|---|---|
| Beta-Carotene | g | 0.2 |
| Compound 1 | g | 1 |
| Cetostearyl alcohol | g | 5 |
| Sodium cetostearyl sulphate | g | 0.5 |
| Dimethicone 350 CST | g | 0.5 |
| Methyl-p-hydroxybenzoate | g | 0.18 |
| Propyl-p-hydroxybenzoate | g | 0.02 |
| Water | g | 92.6 |

The invention claimed is:

1. A complex between a glycogen-based polymer comprising at least one repeating unit represented by formula (I)

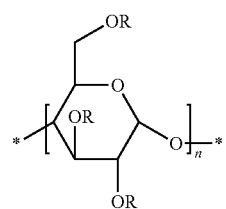

wherein
each group R, which may be identical or different, is a hydrogen atom, an alkyl group having from 1 to 12 carbon atoms, an alkenyl group having from 2 to 12 carbon atoms, an arylalkyl group having from 7 to 18 carbon atoms, or an arylalkenyl group having from 8 to 18 carbon atoms, the alkyl or alkenyl chain of said groups being optionally interrupted by an oxygen atom and not being substituted by a hydroxyl group, and the aryl residue of said groups being optionally substituted by a halogen atom, provided that at least one of said R group is different from hydrogen, and
n is an integer greater than 1, wherein said polymer has a molecular weight of at least 2.5×10⁶ daltons, and a lipophilic compound selected from the group consisting of a BCS class II drug, a BCS class IV drug, and a carotenoid.

2. The complex according to claim 1, wherein said lipophilic compound is selected from the group consisting of a BCS class II drug and a BCS class IV drug.

3. The complex according to claim 2, wherein said lipophilic compound is a BCS class II drug selected from the group consisting of amiodarone, atorvastatin, azithromycin, carbamazepine, carvedilol, celecoxib, chlorpromazine, cisapride, ciprofloxacin, cyclosporine, danazol, dapsone, diclofenac, diflunisal, digoxin, erythromycin, flurbiprofen, glipizide, glyburide, griseofulvin, ibuprofen, indinavir, indomethacin, itraconazole, ketoconazole, lansoprazolel, lovastatin, mebendazole, naproxen, nelfinavir, ofloxacin, oxaprozin, phenazopyridine, phenytoin, piroxicam, raloxifene, repaglinide, ritonavir, saquinavir, sirolimus, spironolactone, tacrolimus, talinolol, tamoxifen, and terfenadine.

4. The complex according to claim 2, wherein said lipophilic compound is a BCS class IV drug selected from the group consisting of amphotericin B, chlorthalidone, chlorothiazide, colistin, ciprofloxacin, docetaxel, furosemide, hydrochlorothiazide, mebendazole, methotrexate, neomycin, and paclitaxel.

5. A complex between a glycogen-based polymer comprising at least one repeating unit represented by formula (I)

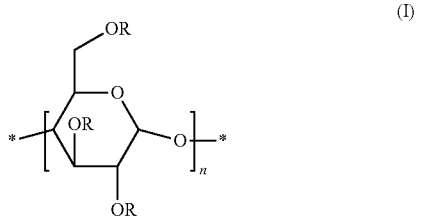

wherein
each group R, which may be identical or different, is a hydrogen atom, an alkyl group having from 1 to 12 carbon atoms, an alkenyl group having from 2 to 12 carbon atoms, an arylalkyl group having from 7 to 18 carbon atoms, or an arylalkenyl group having from 8 to 18 carbon atoms, the alkyl or alkenyl chain of said groups being optionally interrupted by an oxygen atom and not being substituted by a hydroxyl group, and the aryl residue of said groups being optionally substituted by a halogen atom, provided that at least one of said R group is different from hydrogen, and
n is an integer greater than 1,
wherein said polymer has a molecular weight of at least 2.5×10⁶ daltons, and a lipophilic compound selected from the group consisting of a carotene, a xanthophyll, an apocarotenoid, a vitamin A retinoid, and a retinoid drug.

6. The complex according to claim 5, wherein said lipophilic compound is a carotene selected from the group comprising α-carotene, β-carotene, γ-carotene, δ-carotene, ε-carotene, lycopene, phytoene, phytofluene, and torulene.

7. The complex according to claim 5, wherein said lipophilic compound is a xanthophyll selected from the group comprising antheraxanthin, astaxanthin, canthaxanthin, citranaxanthin, cryptoxanthin, diadinoxanthin, diatoxanthin, dinoxanthin, flavoxanthin, fucoxanthin, lutein, neoxanthin, rhodoxanthin, rubixanthin, violaxanthin and zeaxanthin.

8. A nutraceutical composition comprising a complex between a glycogen-based polymer comprising at least one repeating unit represented by formula (I)

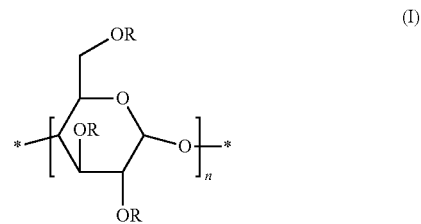

wherein
each group R, which may be identical or different, is a hydrogen atom, an alkyl group having from 1 to 12 carbon atoms, an alkenyl group having from 2 to 12 carbon atoms, an arylalkyl group having from 7 to 18 carbon atoms, or an arylalkenyl group having from 8 to 18 carbon atoms, the alkyl or alkenyl chain of said groups being optionally interrupted by an oxygen atom and not being substituted by a hydroxyl group, and the aryl residue of said groups being optionally substituted by a halogen atom, provided that at least one of said R group is different from hydrogen, and
n is an integer greater than 1,
wherein said polymer has a molecular weight of at least 2.5×10⁶ daltons, a carotenoid, and at least one nutraceutically acceptable excipient.

9. A cosmetic composition comprising a complex between a glycogen-based polymer comprising at least one repeating unit represented by formula (I)

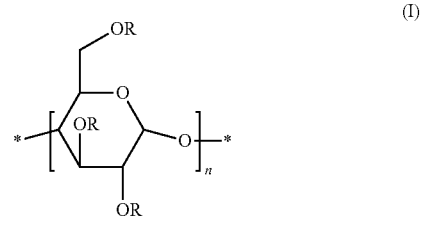

wherein
each group R, which may be identical or different, is a hydrogen atom, an alkyl group having from 1 to 12 carbon atoms, an alkenyl group having from 2 to 12 carbon atoms, an arylalkyl group having from 7 to 18 carbon atoms, or an arylalkenyl group having from 8 to 18 carbon atoms, the alkyl or alkenyl chain of said groups being optionally interrupted by an oxygen atom and not being substituted by a hydroxyl group, and the aryl residue of said groups being optionally substituted by a halogen atom, provided that at least one of said R group is different from hydrogen, and
n is an integer greater than 1,
wherein said polymer has a molecular weight of at least 2.5×10⁶ daltons, a carotenoid, and at least one cosmetically acceptable excipient.

10. A method of enhancing the solubility in water of a lipophilic compound, comprising forming a complex between said lipophilic compound and a polymer comprising at least one repeating unit represented by formula (I)

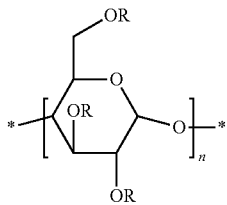

(I)

wherein
each group R, which may be identical or different, is a hydrogen atom, an alkyl group having from 1 to 12 carbon atoms, an alkenyl group having from 2 to 12 carbon atoms, an arylalkyl group having from 7 to 18 carbon atoms, or an arylalkenyl group having from 8 to 18 carbon atoms, the alkyl or alkenyl chain of said groups being optionally interrupted by an oxygen atom and not being substituted by a hydroxyl group, and the aryl residue of said groups being optionally substituted by a halogen atom, provided that at least one of said R group is different from hydrogen, and
n is an integer greater than 1,
wherein said polymer has a molecular weight of at least $2.5 \times 10^6$ daltons, wherein said lipophilic compound is selected from the group consisting of a BCS class II drug, a BCS class IV drug, and a carotenoid.

11. A method of administering a lipophilic compound, comprising administering a complex between said lipophilic compound and a polymer comprising at least one repeating unit represented by formula (I)

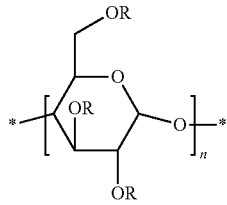

(I)

wherein
each group R, which may be identical or different, is a hydrogen atom, an alkyl group having from 1 to 12 carbon atoms, an alkenyl group having from 2 to 12 carbon atoms, an arylalkyl group having from 7 to 18 carbon atoms, or an arylalkenyl group having from 8 to 18 carbon atoms, the alkyl or alkenyl chain of said groups being optionally interrupted by an oxygen atom and not being substituted by a hydroxyl group, and the aryl residue of said groups being optionally substituted by a halogen atom, provided that at least one of said R group is different from hydrogen, and
n is an integer greater than 1,
wherein said polymer has a molecular weight of at least $2.5 \times 10^6$ daltons, wherein said lipophilic compound is selected from the group consisting of a poorly water soluble drug, a carotenoid BCS class II drug, a BCS class IV drug, and a carotenoid.

* * * * *